United States Patent
Huang et al.

(10) Patent No.: US 10,687,902 B2
(45) Date of Patent: Jun. 23, 2020

(54) SURGICAL NAVIGATION SYSTEM AND AUXILIARY POSITIONING ASSEMBLY THEREOF

(71) Applicant: EPED Inc., Kaohsiung (TW)

(72) Inventors: Ta-Ko Huang, Kaohsiung (TW); Jerry T. Huang, Kaohsiung (TW)

(73) Assignee: EPED, Inc., Kaohsiung (TW)

( * ) Notice: Subject to any disclaimer, the term of this patent is extended or adjusted under 35 U.S.C. 154(b) by 95 days.

(21) Appl. No.: 15/990,366

(22) Filed: May 25, 2018

(65) Prior Publication Data

US 2018/0338798 A1 Nov. 29, 2018

(30) Foreign Application Priority Data

May 26, 2017 (CN) .................................. 106117710

(51) Int. Cl.
*A61B 34/20* (2016.01)
*A61B 90/50* (2016.01)

(52) U.S. Cl.
CPC .............. *A61B 34/20* (2016.02); *A61B 90/50* (2016.02); *A61B 2034/2055* (2016.02); *A61B 2034/2068* (2016.02); *A61B 2034/2072* (2016.02); *A61B 2090/502* (2016.02)

(58) Field of Classification Search
CPC ...... A61B 2034/2068; A61B 2090/502; A61B 34/20; A61B 90/50; A61B 2034/2055; A61B 2034/2072
See application file for complete search history.

(56) References Cited

U.S. PATENT DOCUMENTS

| 5,971,997 A * | 10/1999 | Guthrie .................. A61B 90/11 606/130 |
| 2002/0042619 A1* | 4/2002 | Dominguez ........... A61B 90/14 606/130 |
| 2011/0174314 A1 | 7/2011 | Miyazaki |
| 2012/0316486 A1 | 12/2012 | Cheung et al. |
| 2015/0239082 A1* | 8/2015 | Krouglicof ........ H02K 41/0356 248/346.01 |

\* cited by examiner

*Primary Examiner* — Mark D Remaly
(74) *Attorney, Agent, or Firm* — Schmeiser, Oslen & Watts LLP

(57) ABSTRACT

The present invention provides a surgical navigation system including a positioning device, a processing device and a display device. The positioning device includes an auxiliary positioning assembly capable of wearing or fixing around a patient's affected part and an optics positioning assembly. The optics positioning assembly can sense the position of the auxiliary positioning assembly to form a positioning information. The processing device can receive the positioning information and integrate the positioning information with a medical image to form a navigation information, so that the navigation information is displayed on the display device through a stereoscopic image or a sectional image. Therefore, the doctor can accurately perform the relevant surgical operations on the patient's affected part through the displayed information.

5 Claims, 4 Drawing Sheets

SURGICAL NAVIGATION SYSTEM AND AUXILIARY POSITIONING ASSEMBLY THEREOF

(a) TECHNICAL FIELD OF THE INVENTION

The present invention relates to a surgical auxiliary device, and more particularly to an auxiliary navigation system capable of displaying the immediate position of the affected part through a device to provide the immediate position for physicians to perform related operations.

(b) DESCRIPTION OF THE PRIOR ART

One of the key factors of determining the success of surgery is whether the doctor can accurately grasp the position of performing the surgery or not, and the relevant surgical operations can be completed by the correct position. For example, if a dentist can drill holes for dental implants in the correct position of the patient's gums and along the correct axis. In other words, if the dentist does not drill the correct hole in the patient's gum, it may cause the problem that the dental implant cannot be correctly placed on the gum, resulting in the failure of the entire implant surgery. Therefore, the dentists will use the patient's dental model in advance to perform related drilling planning before surgery. However, it is still that the drilling position is determined by the dentist when the operation is performed. Hence, it is still easy to cause problem that the position of the drilling hole is incorrect, resulting in surgery failure.

Therefore, some manufacturers nowadays have developed a surgical navigation system that disposed positioning members on the patient's affected part and the doctor's hand tools; these positioning members are positioned by an optics positioning method; and then the information of the affected part of the patient is integrated to display on the display device. Therefore, the doctor can complete the surgical plan in the affected part of the patient through the assistance of the navigation screen.

However, in an actual implementation, the positioning member disposed on the affected part of the patient (in the case of teeth-related surgery, namely, the mouth) cannot be removed from the affected part after the optics positioning is completed, so as to avoid the possibility of repositioning during the surgery. However, the operation of the device is hindered because of the positioning members on the affected part of the patient when the doctor or the related assistants carry out the operation.

Therefore, the inventor has devoted himself to the research and application of theories, and has proposed an invention that is rational in design and effectively improves the above problems.

SUMMARY OF THE INVENTION

The main purpose of the present invention is to provide a surgical navigation system and auxiliary positioning assembly thereof, so as to solve the problem that the positioning member used for assisting positioning in the prior art may cause obstacles to the doctor or related assistants.

In order to achieve the above purpose, the present invention provides a surgical navigation system for assisting an operator in positioning a patient's affected part, and the surgical navigation system comprises a positioning device, a processing device and a display device. The positioning device comprises an auxiliary positioning assembly, a positioning member, a hand tool positioning member and an optics positioning assembly. The auxiliary positioning assembly comprises a wearing member, a connecting seat and an auxiliary positioning member. The wearing member may be worn or fixed adjacent to the affected part of the patient, and the wearing member can be synchronously moved or rotated based on affected part. The connecting seat is fixedly disposed on the wearing member. The auxiliary positioning member is connected to the connecting seat, and the auxiliary positioning member is rotated relative to the connecting seat, and the auxiliary positioning member has a plurality of auxiliary positioning marks. The positioning member is fixedly disposed on the affected part of the patient and comprises a plurality of positioning holes. The hand tool positioning member is used for fixedly disposing on a hand tool, and the hand tool may be a surgical instrument or a probe. The hand tool positioning member comprises a plurality of hand tool positioning marks. The optics positioning assembly comprises a plurality of sensing units which can sense the position of the auxiliary positioning marks and the position of the hand tool positioning marks during the hand tools extending into the positioning holes in sequence to form a positioning information correspondingly. The processing device is used for storing a medical image of the patient and is electrically connected to the optics positioning assembly to receive the positioning information; wherein the processing device can integrate the medical image with the positioning information to form a navigation information. The display device is electrically connected to the processing device to display the navigation information or to display the location of the device and the surrounding image through a stereoscopic image or a sectional image.

Preferably, the auxiliary positioning member further comprises a connecting member detachably disposed on the connecting seat, and the auxiliary positioning member is rotatablely disposed on the connecting member. Further, a shielding member may be selectively sandwiched between the connecting member and the connecting seat, and the shielding member may correspondingly shield at least part of the head of the patient. The shielding member may be a surgical towel to separate the sterilized area from the unsterile area.

Preferably, the connecting seat and the connecting member respectively have magnetic units, and the magnetic unit of the connecting seat is opposite to the magnetic unit of the connecting member. Further, the magnetic unit of the connecting member may be attracted to the magnetic unit of the connecting seat, so that the connecting member may be fixedly disposed on the connecting seat.

Preferably, the auxiliary positioning assembly further comprises a rotating pivot member pivoting on the connecting member so as to be rotatable relative to the connecting member, and the auxiliary positioning member is fixedly disposed on the rotating pivot member and may rotate with the rotating pivot member relative to the connecting member.

Preferably, the optics positioning assembly further comprises a plurality of laser units. The processing device is electrically connected to the optics positioning assembly. The processing device controls the laser unit to emit laser light to the patient according to the integrated information so as to complete the relevant mechanical installation.

In order to achieve the above purpose, the present disclosure further provides an auxiliary positioning assembly for providing an optics positioning assembly for positioning an appropriate position around a user's affected part, and the auxiliary positioning assembly comprises a wearing member, a connecting seat and an auxiliary positioning member.

The wearing member may be worn or fixed adjacent to the affected part of the patient, and the wearing member may be synchronously moved or rotated with affected part. The connecting seat is fixedly disposed on the wearing member. The auxiliary positioning member is connected to the connecting seat, and the auxiliary positioning member may be rotated relative to the connecting seat, and the auxiliary positioning member has a plurality of auxiliary positioning marks; wherein the optics positioning assembly may mark the auxiliary positioning member through the auxiliary positioning marks.

Preferably, the auxiliary positioning member further comprises a connecting member detachably disposed on the connecting seat, and the auxiliary positioning member is rotatably disposed on the connecting member. Further, a shielding member may be selectively sandwiched between the connecting member and the connecting seat to separate the sterilized area from the unsterile area.

Preferably, the connecting seat and the connecting member respectively have magnetic units, and the magnetic unit of the connecting seat is opposite to the magnetic unit of the connecting member. Further, the magnetic unit of the connecting member may be attracted to the magnetic unit of the connecting seat, so that the connecting member may be fixedly disposed on the connecting seat.

Preferably, the auxiliary positioning member further comprises a rotating pivot member pivoting on the connecting member so as to be rotatable relative to the connecting member, and the auxiliary positioning member is fixedly disposed on the rotating pivot member and may rotate with the rotating pivot member relative to the connecting member.

The beneficial effects of the present invention may be that the auxiliary positioning function can be achieved through the installation of the auxiliary positioning assembly, and the auxiliary positioning assembly is not the obstacle when the doctor or the assistant pass the devices or perform surgery during the operation.

These and other objectives of the present invention will undoubtedly become obvious to those of ordinary skill in the art after reading the following detailed description of the preferred embodiment that is illustrated in the various figures and drawings.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Figure 1:
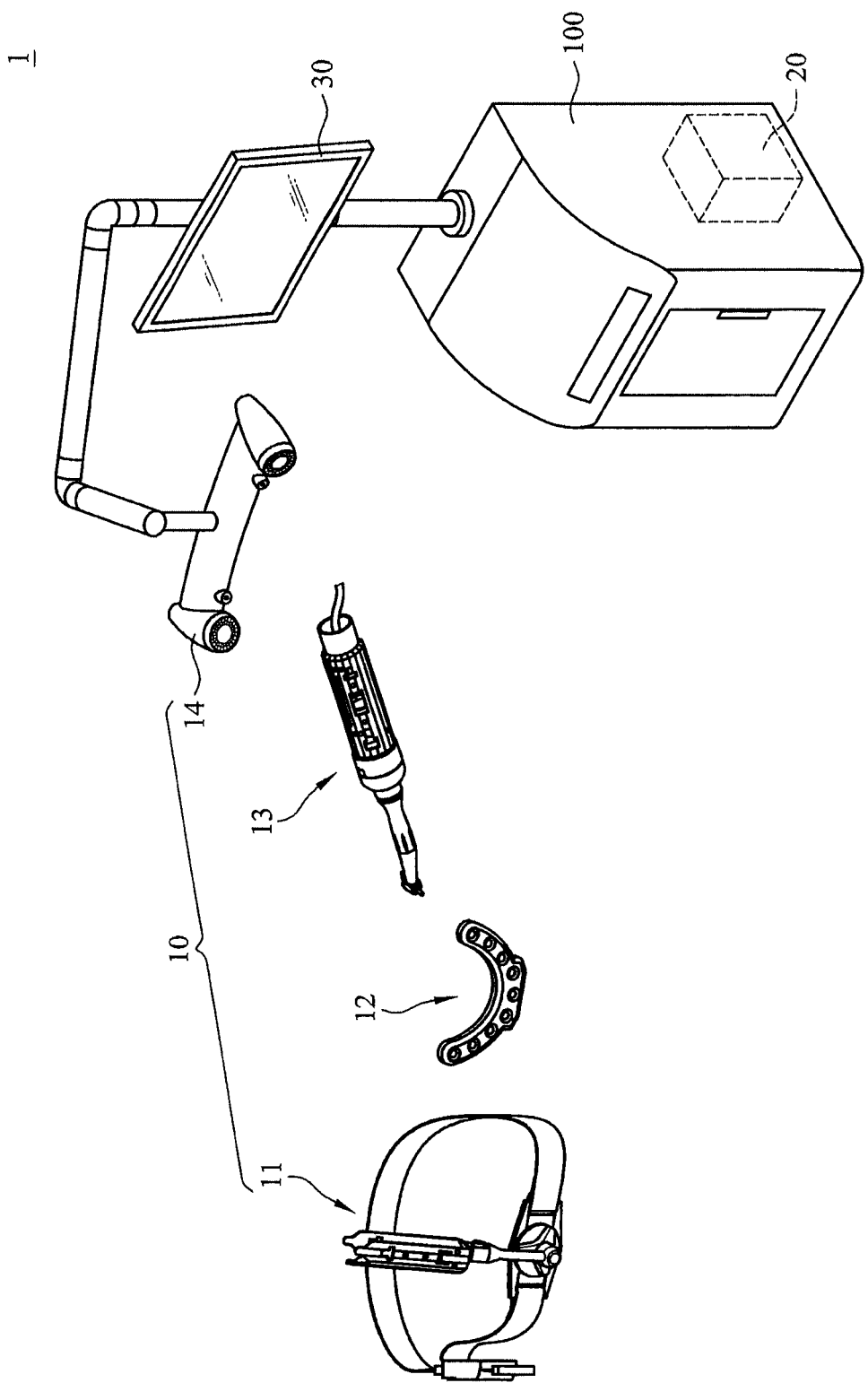
FIG. 1 is a schematic view of a surgical navigation system according to the present invention.

In the following paragraphs, a detailed description is provided for a thorough understanding of the figures listed above. Well-known structures and devices will also be used schematically for better comprehension.

Please refer to FIG. 1 to FIG. 4, FIG. 1 to FIG. 4 are schematic views of a surgical navigation system according to the present invention. In order to make the description of this embodiment easier to understand, the dental surgery is taken as an example, but the present invention is not limited thereto.

As shown in FIG. 1 to FIG. 4, the surgical navigation system 1 comprises a positioning device 10, a processing device 20 and a display device 30. The positioning device 10 and the display device 30 are respectively electrically connected to the processing device 20 and can communicate information with the processing device 20. The positioning device 10 comprises an auxiliary positioning assembly 11, a positioning member 12, a hand tool positioning member 13 and an optics positioning assembly 14.

Please refer to FIG. 1, the surgical navigation system 1 may further include a mechanism body 100 in practical applications. The optics positioning assembly 14, the processing device 20, and the display device 30 may be disposed on the mechanism body 100; wherein the processing device 20 may be, for example, various types of computers.

Figure 2:
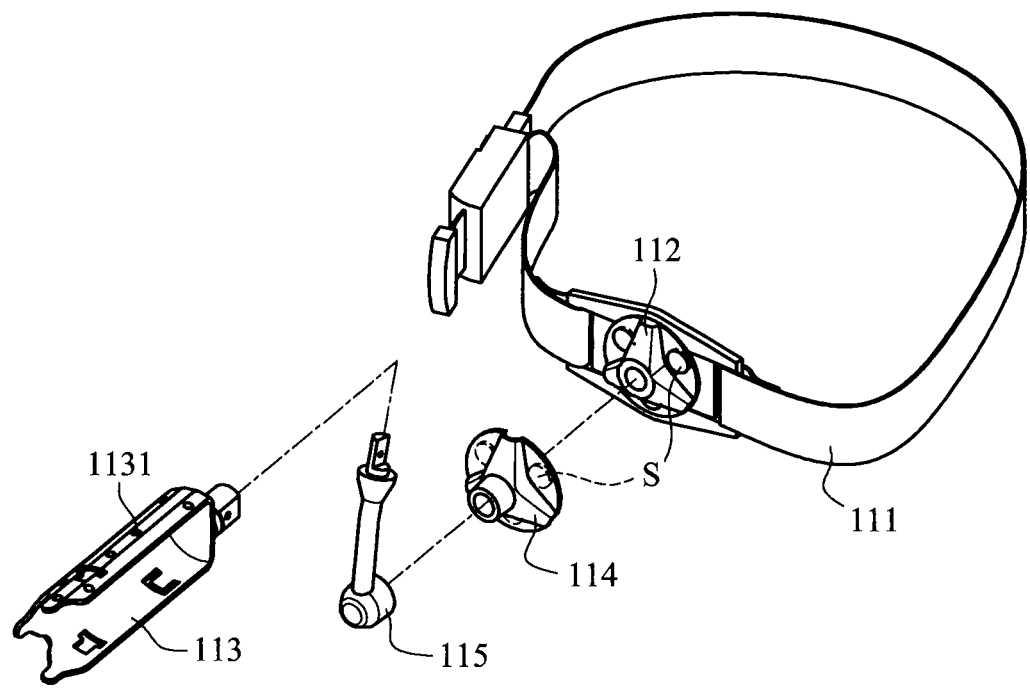
FIG. 2 and FIG. 3 are schematic views of partial components of a positioning device of the surgical navigation system applied to a patient according to the present invention.
Figure 3:
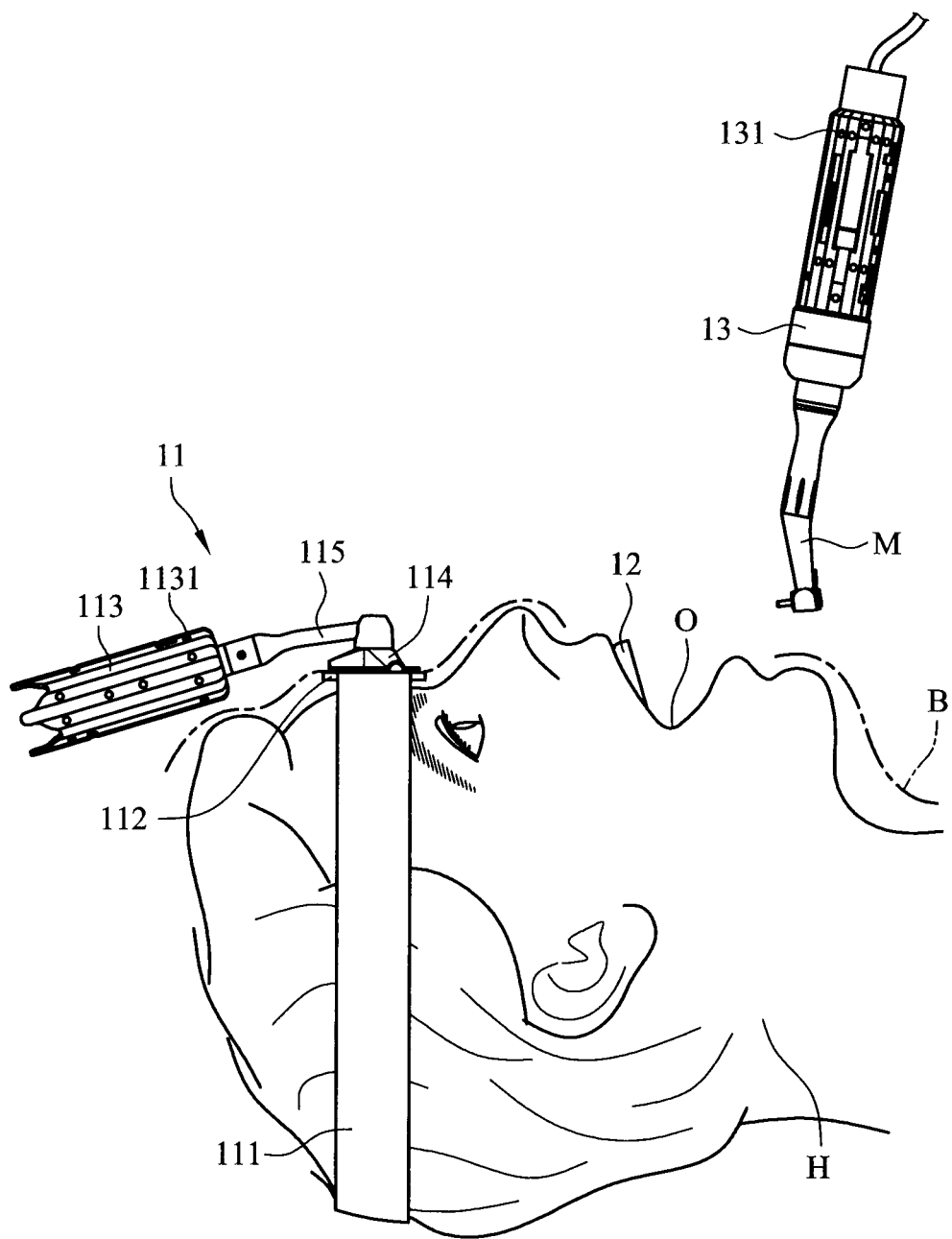

Please refer to FIG. 2, FIG. 2 is an exploded schematic view of the auxiliary positioning assembly 11. As shown in FIG. 2, the auxiliary positioning assembly 11 comprises a wearing member 111, a connecting seat 112, an auxiliary positioning member 113, a connecting member 114, a rotating pivot member 115 and a plurality of magnetic units S. The wearing member 111 may be a belt body with two ends selectively connectable, for example, it may be a fastening structure, and it may be directly worn around the patient's affected part H (as shown in FIG. 2 and FIG. 3, the surroundings relative to the mouth may be the head), which can be synchronously rotated or moved with the affected part O. A connecting seat 112 is disposed on the wearing member 111, and the connecting member 114 may be detachably disposed on the connecting seat 112, and a rotating pivot member 115 may be pivoted on the connecting member, and the auxiliary positioning member 113 is fixedly disposed on the rotating pivot member 115. Therefore, the auxiliary positioning member 113 may be connected and disposed on the wearing member 111, and the auxiliary positioning member 113 may be rotated relative to the connecting member 114, the connecting seat 112 and the wearing member 111. A plurality of auxiliary positioning marks 1131 is disposed on the auxiliary positioning member 113. The plurality of auxiliary positioning marks 1131, for example, may be a light-emitting unit or a light-reflective unit to assist the optics positioning unit 14 to perform positioning of the auxiliary positioning unit 113.

In this embodiment, the connecting member 114 and the connecting seat 112 may respectively have magnetic units S, and both of them may be attracted and fixed to each other through the magnetic units S, whereby a shielding member B may be sandwiched between the connecting member 114 and the connecting seat 112, and the connecting member 114 may be quickly and easily separated from the connecting seat 112 according to user requirements (to dispose or replace the shielding member B). Of course, in other applications, the connecting member 114 and the connecting seat 112 may respectively have a corresponding fastening structure (not shown) or a rapid disassembling mechanism (not shown), and both of the connecting member 114 and the connecting seat 112 may be rapidly disassembled through the corresponding fastening structure or the corresponding rapid disassembling mechanism. In practical applications, the shielding member B may be a disinfecting towel that may separate the sterilized area from the unsterile area. The connecting member 114 and the connecting seat 112 may respectively have corresponding connecting structures so as to strengthen the connecting force between the connecting member 114 and the connecting seat 112. Furthermore, the combination of two items through the fastening structure or the rapid disassembling mechanism is derived from the combination of the conventional mechanism; therefore, the structures are not described here. The fastening structure or the rapid disassembling mechanism could be easily achieved by a person who has common technical knowledge in the field.

A rotating pivot member 115 may be rotatably disposed on the connecting member 114; therefore, the auxiliary positioning member 113 fixed to the rotating pivot member 115 may be rotated relative to the wearable member 111. After the operator completes positioning through the auxiliary positioning marks 1131 of the auxiliary positioning member 113, the operator can turn the auxiliary positioning member 113 to other positions to prevent the auxiliary positioning member 113 from interfering with the operation. Because the auxiliary positioning assembly 11 is worn around the affected part H of the patient (in this embodiment, namely, the head), the possibility of affecting the operation has been greatly reduced compared with the conventionally installed in mouth of the patient.

Specifically, in other embodiments, the auxiliary positioning assembly 11 may only comprise the wearing member 111, the connecting seat 112, and the auxiliary positioning member 113, and the auxiliary positioning member 113 may be directly rotatable and connected to the connecting seat 112, but the present invention is not limited thereto. It is worth mentioning that, in practical applications, the connecting members may be disposed between the connecting member 114 and the rotating pivotal member 115 so as to strengthen the mechanical connecting force between them, so that the auxiliary positioning member 113 may be stably connected to the rotating pivotal member 115 during optical positioning. Of course, in a better application, a limiting member (not shown) may also be disposed between the rotating pivotal member 115 and the connecting member 114, so that the rotating pivotal member 115 cannot be rotated relative to the connecting member 114 during optics positioning to improve the stability of optical positioning.

Figure 4:
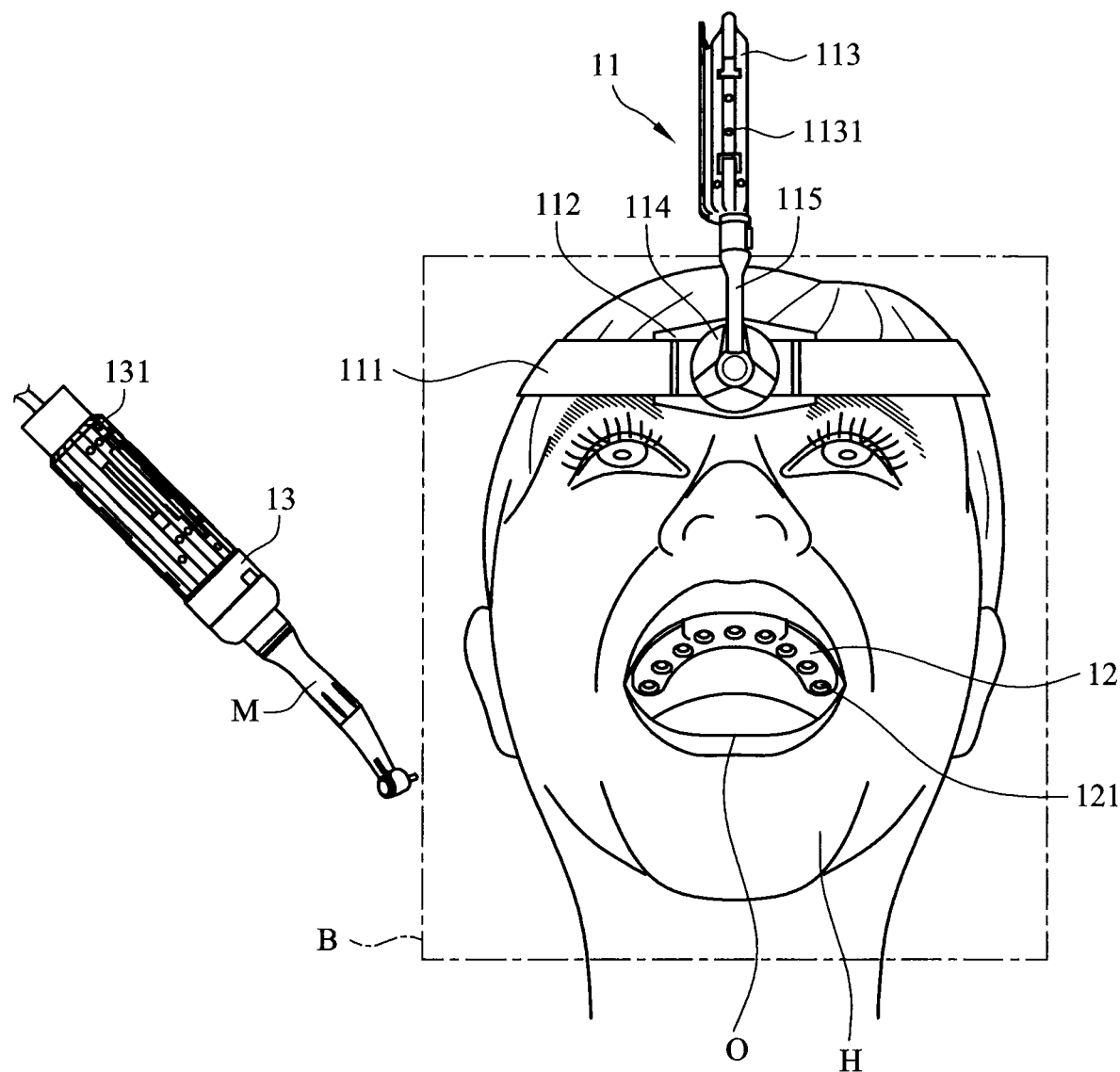
FIG. 4 is an exploded schematic view of an auxiliary positioning member according to the present invention.

Please refer to FIG. 3 and FIG. 4, FIG. 3 and FIG. 4 are schematic views of the auxiliary positioning component 11, the positioning member 12 and the hand tool positioning member 13 applied to implant surgery. As shown in FIG. 3 and FIG. 4, the auxiliary positioning assembly 11 is fixedly disposed around the affected part H of the patient (that is, corresponds to the head), the positioning member 12 is disposed on the affected part O of the patient (in this embodiment, namely, the mouth), and the hand tool positioning member 13 is fixedly disposed on the hand tools M (such as drills or probes) of the doctors. The positioning member 12 comprises a plurality of positioning holes 121 spaced apart from each other. The hand tool positioning marks 131 may be, for example, light-emitting units or light-reflective units.

Thereby, after the hand tools M extend into the positioning holes 121 in sequence, the position of the auxiliary positioning marks 1131 and the positions of the hand tool positioning marks 131 are sensed so as to generate a positioning information correspondingly by means of optics positioning assembly 14 (as shown in FIG. 1) with a plurality of sensing units 141 (such as image capturing unit). Specifically, the optics positioning assembly 14 may simulate positioning information with three dimensions through the three reference points of the auxiliary positioning marks 1131, the hand tool positioning marks 131, and the positioning holes 121.

After the positioning is completed by the optics positioning assembly 14, the processing device 20 will receive the positioning information, and the patient's medical image is stored in the processing device 20. In this embodiment, the patient's medical image is the tooth information; therefore, the positioning information is integrated with the patient's medical image to form a navigation information, so that the navigation information is displayed or displayed the position of the device and the surrounding images by stereoscopic images or cross-sectional images in the display device 30 to assist the doctor in performing surgery. Specifically, the medical image may be a tomogram and a 3D mimic diagram of the patient, and the processing device 20 further cooperates with the three-dimensional positioning information generated by the optics positioning component 14 to accurately display the navigation information in the display. The position of the doctor's hand tool M is currently positioned; thereby the surgical navigation system can effectively assist doctors in drilling operations.

In a preferred embodiment, the optics positioning assembly 14 further comprises a plurality of laser units 142. The aiming operation is completed by laser spot emitted from the laser unit 142 to facilitate the installation of the devices.

In summary, the surgical navigation system of the present invention may effectively assist the doctor in positioning the drilling position during implant surgery, thereby effectively improving the accuracy of the drilling position. Simultaneously, the design of the auxiliary positioning device not only can effectively perform optical positioning but also does not affect the operation during the operation.

The above descriptions for each figure explain the principles of the disclosure and its practical applications. The embodiments depicted above and the appended drawings are exemplary and are not intended to be exhaustive or to limit the scope of the disclosure. Modifications and variations are possible in view of the above teachings.

The invention claimed is:

1. A surgical navigation system for assisting an operator in positioning a surgical site of a patient, the surgical navigation system comprising:
 a positioning device comprising:
  an auxiliary positioning assembly comprising:
   a wearing member configured to be fixedly coupled to the patient at a location adjacent the surgical site of the patient, wherein the wearing member moves in sync with the surgical site in response to movement of the surgical site;
   a connecting seat coupled to the wearing member; and
   an auxiliary positioning member rotatably coupled to the connecting seat, the auxiliary positioning member comprising a plurality of auxiliary positioning marks thereon, wherein each of the plurality of auxiliary positioning marks is selected from the group consisting of a light-emitting unit and a light-reflective unit;
  a positioning member configured to be fixedly coupled directly to and engage the surgical site of the patient, separate from the auxiliary positioning assembly, the positioning member comprising a plurality of positioning holes therethrough, wherein each of the plurality of positioning holes is configured to receive a hand tool inserted partially therethrough;

a hand tool positioning member configured to be fixedly coupled to a hand tool, the hand tool positioning member comprising a plurality of hand tool positioning marks, wherein each of the plurality of hand tool positioning marks is selected from the group consisting of a light-emitting unit and a light-reflective unit; and an optics positioning assembly comprising a plurality of sensing units configured to sense the position of each of the plurality of auxiliary positioning marks and the position of each of the plurality of hand tool positioning marks while a hand tool, to which the hand tool positioning member is coupled, is partially extended into each of the plurality of positioning holes, in sequence, to generate a corresponding positioning information, wherein the positioning information includes the location and orientation of each of the auxiliary positioning member and the hand tool positioning member correspondingly;

a processing device for storing a medical image of the patient and coupled to the optics positioning assembly to receive the positioning information, wherein the processing device is configured to integrate the medical image with the positioning information to form a navigation information; and a display device coupled to the processing device, the display device being configured to display the navigation information.

2. The surgical navigation system of claim 1, further comprising:

a connecting member detachably coupled to the connecting seat, the auxiliary positioning member being rotatably coupled to the connecting member; and a shielding member configured to be sandwiched between the connecting member and the connecting seat, wherein the shielding member is configured to shield at least a portion of the patient.

3. The surgical navigation system of claim 2, wherein the connecting seat comprises at least one magnet and the connecting member comprises at least one magnet corresponding to the at least one magnet of the connecting seat, wherein the connecting seat is configured to be magnetically coupled to the connecting member by attraction of the at least one magnet of the connecting seat and the corresponding at least one magnet of the connecting member through the shielding member.

4. The surgical navigation system of claim 3, further comprising a rotating pivot member coupled between the connecting member and the auxiliary positioning member, wherein the rotating pivot member is rotatable with respect to the connecting member and fixedly coupled to the auxiliary positioning member.

5. The surgical navigation system of claim 2, wherein each of the connecting seat and the connecting member, respectively, has one of a fastening mechanism and a rapid disassembling mechanism, the fastening mechanism being disposed opposite the rapid disassembling mechanism, whereby the connecting member is fixedly and removably coupled to the connecting seat.

* * * * *